USO05305739A

United States Patent [19]
Gray

[11] Patent Number: 5,305,739
[45] Date of Patent: Apr. 26, 1994

[54] INFLATABLE RESUSCITATION DEVICE

[75] Inventor: Thomas C. Gray, Clarkston, Wash.

[73] Assignee: Grayco, Inc., Clarkston, Wash.

[21] Appl. No.: 951,984

[22] Filed: Sep. 28, 1992

[51] Int. Cl.$^5$ ............................................. A61M 15/00
[52] U.S. Cl. .......................... 128/205.13; 128/205.16;
128/205.25; 128/206.28; 417/473; 417/478
[58] Field of Search ............... 417/473, 389, 478;
128/727, 728, 204.18, 203.11, 205.13, 205.16,
205.25, 206.21, 206.28, 28, 202.26

[56] References Cited

U.S. PATENT DOCUMENTS

| | | | |
|---|---|---|---|
| 3,063,620 | 11/1962 | Black | 417/478 |
| 3,356,100 | 12/1967 | Seeler | 137/512.4 |
| 4,521,166 | 6/1985 | Phillips | 417/478 |
| 4,536,136 | 8/1985 | Lan | 417/389 |
| 5,005,568 | 4/1991 | Loescher | 128/202.28 |
| 5,016,625 | 5/1991 | Hsu | 128/201.25 |
| 5,121,745 | 6/1992 | Israel | 128/202.28 |
| 5,133,344 | 7/1992 | Jurrius | 128/201.23 |
| 5,146,914 | 9/1992 | Sturrock | 128/203.11 |

Primary Examiner—Edgar S. Burr
Assistant Examiner—Eric P. Raciti
Attorney, Agent, or Firm—Frederick Gotha

[57] ABSTRACT

A pulmonary resuscitator is set forth of the type having a compressible bladder to be depressed to supply air to a mask. Both the compressible bladder and mask have integral therewith a network of inflatable tubes which when pressurized resiliently rigidify the bladder and mask to establish nominal erected bladder and mask shapes. The bladder has an inlet check valve and the mask has an outlet check valve where the outlet check valve utilizes a flapper valve for permitting flow of fluid into the mask upon depression of the bladder. Exhaust ports are located adjacent the flapper valve and are closed by the flapper valve when the bladder is depressed. The exhaust ports are opened when the flapper valve closes as the bladder returns to its nominal shape after being depressed. An air spring contained within the bladder chamber which is in fluid communication with the network of inflatable tubes through limiting orifices controls the rate at which the bladder returns to its nominal shape after depression.

18 Claims, 8 Drawing Sheets

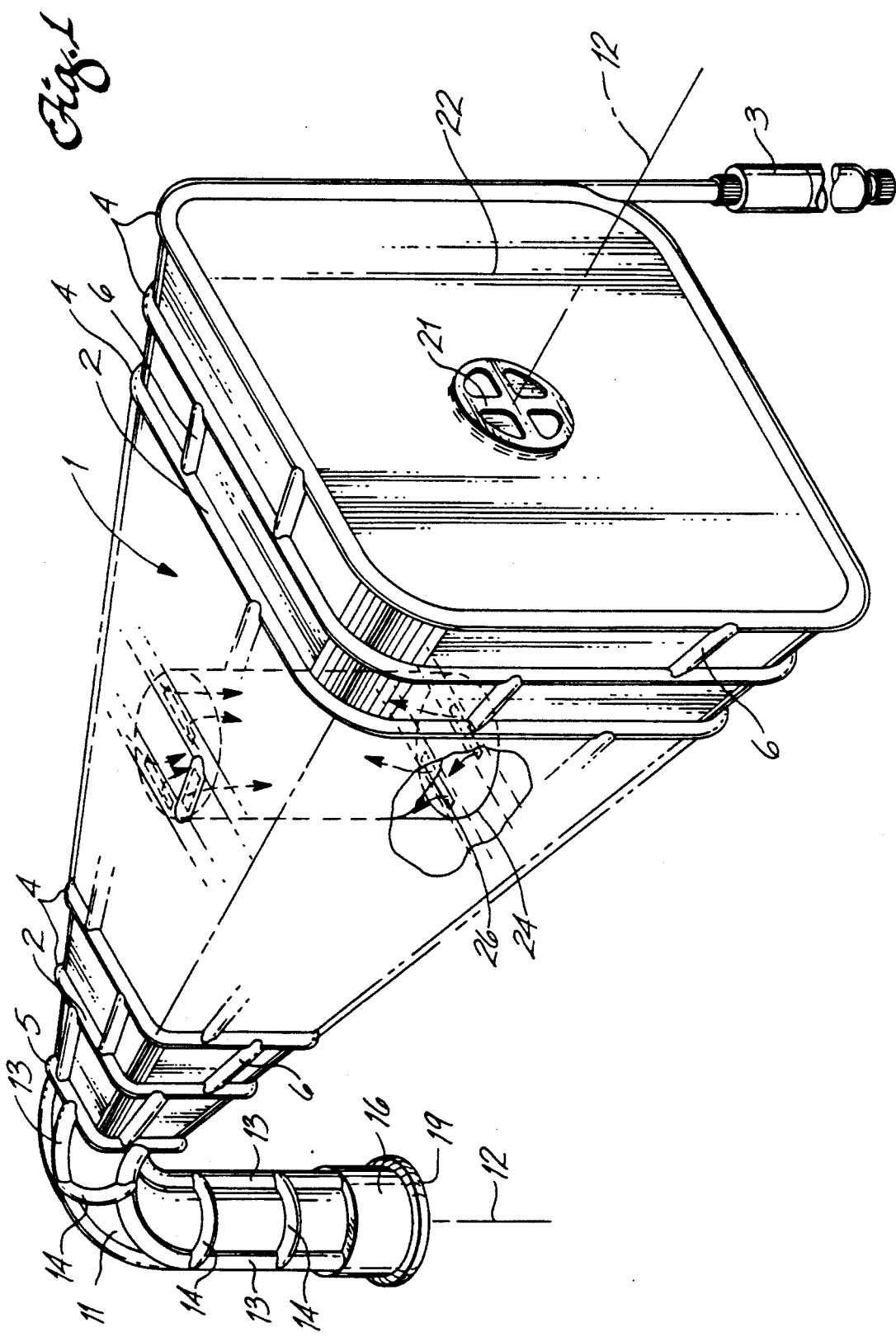

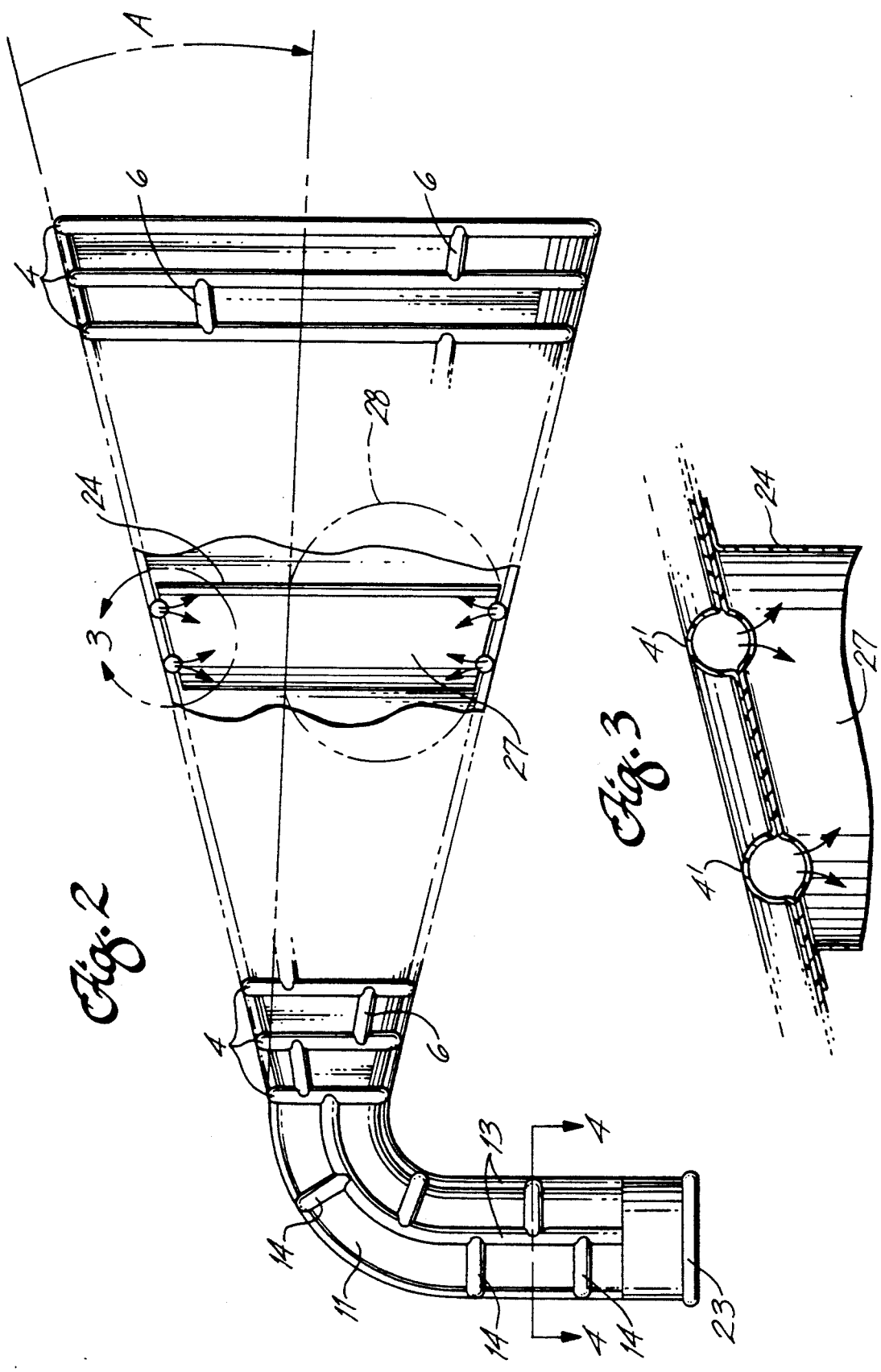

INFLATABLE RESUSCITATION DEVICE

FIELD OF THE INVENTION

This invention relates to an inflatable pulmonary resuscitator where both the face mask and bladder pump members which comprise the device are inflatable.

BACKGROUND OF THE INVENTION

In emergency cardio-pulmonary resuscitation mouth-to-mouth respiration is employed to restore cardiac output and pulmonary ventilation following cardiac arrest and apnea. Mouth-to-mouth resuscitation is a method of artificial ventilation involving an overlap of the patient's mouth with the operator's mouth to inflate the patient's lungs by blowing, followed by an unassisted expiratory phase brought about by elastic recoil of the patient's chest and lungs. Emergency mouth-to-mouth resuscitation requires this procedure to be repeated twelve to sixteen times a minute and therefore exposes a person administering the artificial respiration to disease. Thus, mouth-to-mouth cardio-pulumonary resuscitation which generally is the first emergency aid available to a patient suffering from cardiac arrest exposes the person performing the mouth-to-mouth respiration to high risk of disease and therefore substantially inhibits the willingness of the person to administer such aid. Medical teams called to such emergencies have resuscitator apparatus which force gas, usually oxygen, into the lungs to produce the artificial ventilation; however, such devices are expensive and not generally available.

Mask devices have also been developed which may be placed over the nose and mouth of the patient; this permitted the administrator of the artificial respiration to blow air into the patient's lungs without mouth-to-mouth contact. Such masks, however, cannot be stored in a relatively small space such as a shirt or jacket pocket and thus are inconvenient to carry. Similarly, resuscitation apparatus comprising a ventilator mask and a manually collapsible gas receptacle such as the resuscitator disclosed in U.S. Pat. No. 5,067,487, likewise, cannot be carried easily in a shirt or jacket pocket because of the limitations inherent in the materials used in the construction of the apparatus.

SUMMARY OF THE INVENTION

There is, therefore, provided according to the present invention, an improved pulmonary resuscitator where both the mask and bladder type pump are inflatable structures which can be stored in a relatively small storage space and therefore conveniently carried in a jacket or shirt pocket.

The present invention is directed to an improved pulmonary resuscitator of the type having a compressible bladder to be depressed to supply air to a mask device where the bladder has integrally contained therein an inflatable continuous fluid channel network which when pressurized resiliently rigidify the bladder to establish a nominal erected bladder shape. The bladder has an inlet check valve and the mask has an outlet check valve where the outlet check valve delivers air when the bladder is depressed and exhausts air from the mask as the bladder returns to its nominal erected shape. Having a construction similar to the bladder, the mask device is made of a flexible plastic material and has integral therewith a network of inflatable fluid channels. In one embodiment of the invention the inflatable fluid channels of the mask are in fluid communication with the network of inflatable channels contained in the bladder; and in another embodiment are separate fluid channels, but in either case, when pressurized, resiliently rigidify the mask to establish a nominal erected mask shape.

An inflatable air spring or biasing tube made of a flexible rubberized silk cloth material is integrally contained within the bladder and is in fluid communication with the inflatable channel network such that when the bladder is depressed air pressure within the bias tube will increase and upon release of the bladder will decrease thereby biasing the bladder to return to its nominal shape. To control the collapse rate of the bias tube, limiting orifices in the inflatable fluid channels in fluid communication with the bias tube are utilized to control the rate at which air will flow from the inflatable channels into the bias tube and from it. An inlet check valve is carried by the bladder which closes when the bladder is depressed. The air within the bladder is then permitted to exhaust through the outlet check valve of the mask. When the force compressing the bladder is released, the bias tube contributes to the rate at which the bladder will return to its original shape and because of the lower air pressure within the bladder chamber after being depressed, the inlet check valve will open to allow ambient air to enter into the bladder chamber.

In the preferred embodiment of this invention, the mask device contains inflatable fluid channels so disposed and arranged such that when the inflatable fluid channels are pressurized, they resiliently rigidify the mask device to establish a nominal erected mask shape. Integrally contained in the mask is a bladder connector portion having a plurality of exhaust ports and a flapper valve located at the inlet orifice of the bladder connector. The compressible bladder in the preferred embodiment has inflatable fluid channels which when pressurized resiliently rigidify the bladder to establish a nominal erected bladder shape; these inflatable fluid channels are separately pressurized from the mask device. The compressible bladder has an integral neck portion formed by inflatable fluid channels which comprise a part of the network of fluid channels. The neck portion is releaseably insertible into the bladder connector portion of the mask device where the neck portion of the bladder is sealingly held to permit relative rotation between the neck portion and bladder connector.

In another embodiment of the invention, the neck portion of the bladder and the bladder connector of the mask are integrally connected to form part of the network of the inflatable fluid channels such that both the mask and bladder fluid channels are in fluid communication and therefore when pressurized form the nominal bladder and nominal mask shapes.

Thus, an inflatable pulmonary resuscitator is provided where nominal bladder and mask shapes are achieved through pressurization of a network of interconnected fluid channels which when pressurized resiliently rigidify and form nominal bladder and mask shapes. The mask device is separately inflatable in one embodiment and has a bladder connector portion which is releasably and sealingly insertible into the neck portion of the bladder to permit the bladder to be rotated and angularly positioned with respect to the mask. The inflatable structure permits the resuscitator to occupy a very small space when deflated and therefore the device can be carried in a pocket, small bag or purse.

BRIEF DESCRIPTION OF THE DRAWINGS

These and other features and advantages will become appreciated as the same become better understood with reference to the following specification, claims and drawings wherein:

FIG. is a perspective view of the compressible bladder of this invention illustrating the fluid channel network.

FIG. 2 is a part broken, side elevational view of FIG. 1.

FIG. 3 is an exploded cross-sectional view of the area 3 shown in FIG. 2.

DETAILED DESCRIPTION

Figure 6:
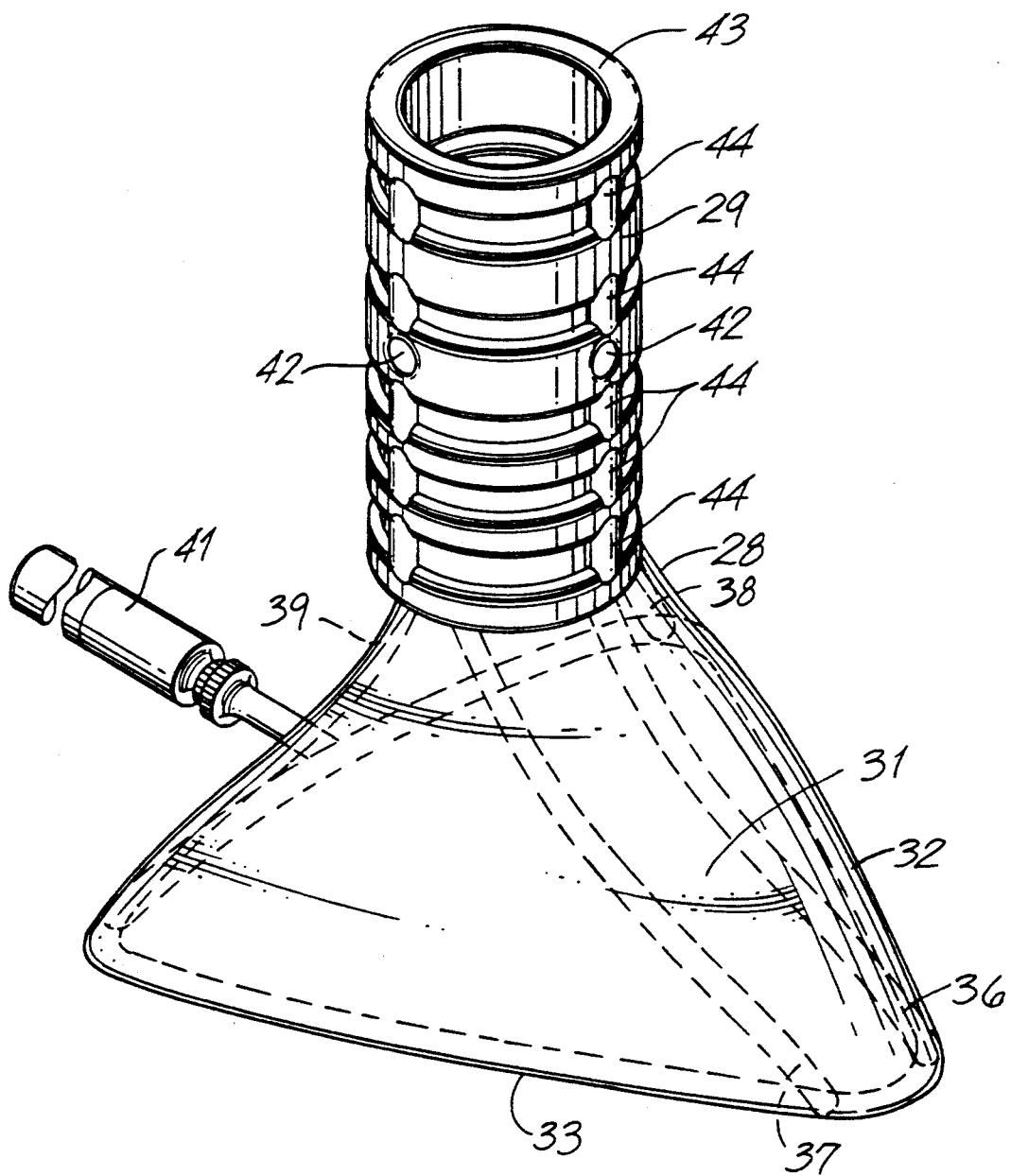
FIG. 6 is a perspective view of one embodiment of the mask device of this invention.
Figure 9:
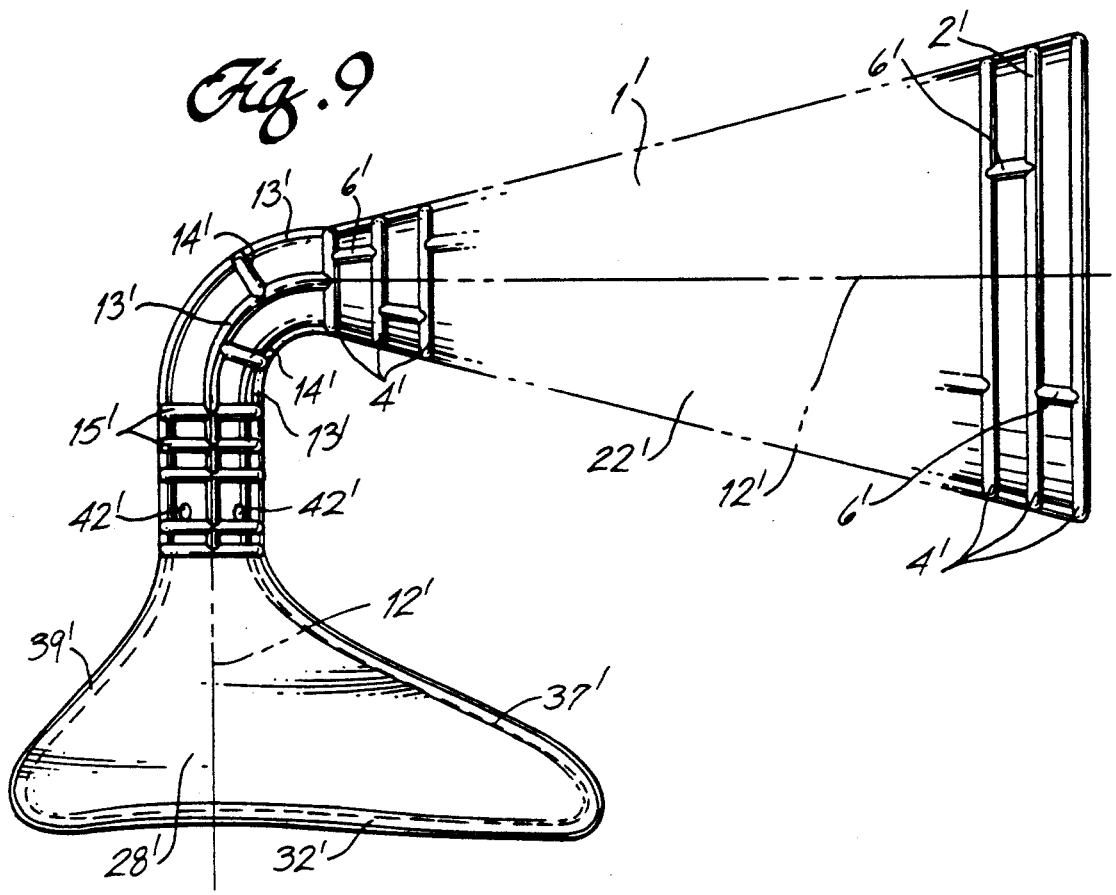
FIG. 9 is an illustration of another embodiment of this invention where the mask and bladder device are integrally connected.

The resuscitation instrument of this invention in the preferred embodiment consists of a bladder or pump member which is separately inflatable for insertion into a user or mask device which is also separately inflatable; the bladder or pump is illustrated in perspective in FIG. and the mask device or user device is shown in perspective after being inflated in FIG. 6. Another embodiment of this invention is shown in FIG. 9 which depicts the resuscitator as a one-piece device having the bladder integrally connected to the mask or user device.

Figure 4:
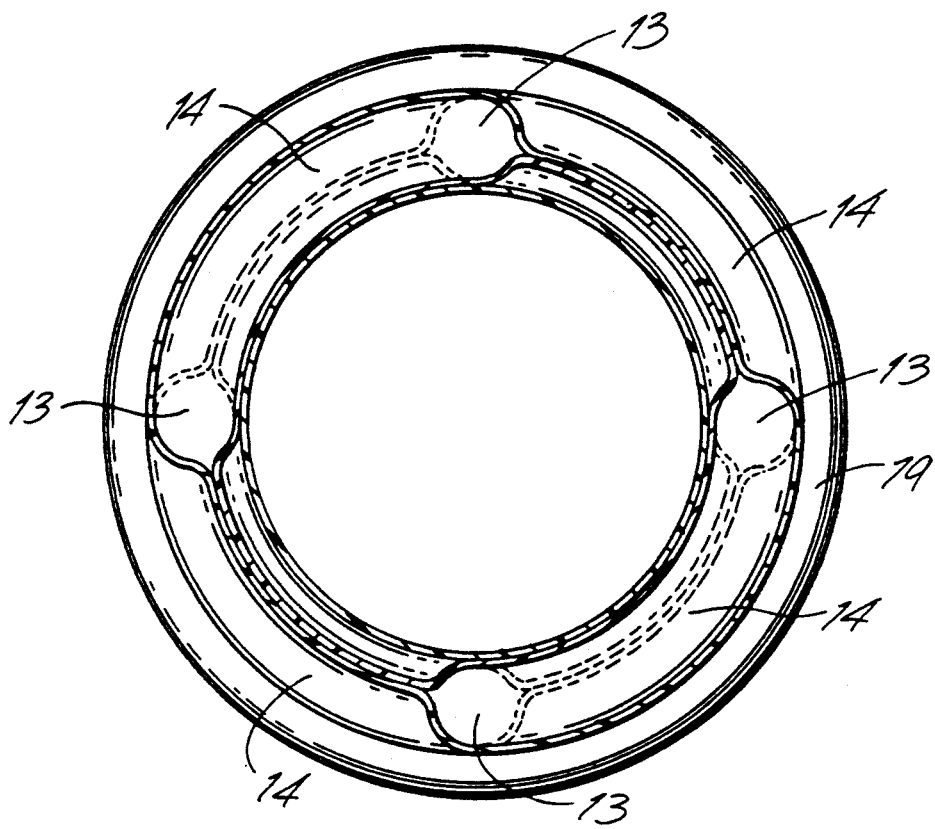
FIG. 4 is a cross-sectional view taken along the line 4—4 of FIG. 2.
Figure 5:
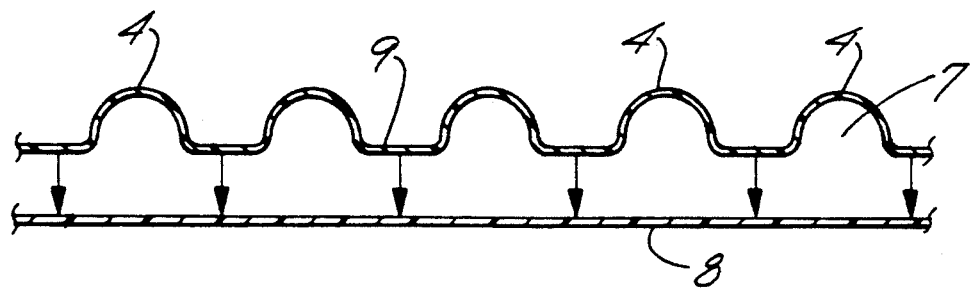
FIG. 5 is a partial cross-sectional view illustrating a joining of materials in the formation of the fluid channels integrally contained in the mask and bladder devices of this invention.

Referring to FIG. the bladder is shown in its nominal erected bladder shape after the network of fluid channels 2 have been pressurized by air which had been stored under pressure in compressed air cannister 3. As can be seen in FIG. the network of fluid channels 2 consists of a plurality of substantially parallel rib members 4 which are in fluid communication with each other through a plurality of axial bridge struts 6 interconnecting the rib members 4. The rib members 4 and the axial bridge struts 6 are integrally formed in a thin grade plastic which is extremely flexible such as a rubberized silk or rubberized cloth or of a rayon or nylon type material. By referring to FIG. 5 the method of construction of the rib members 4 and axial bridge struts 6 is illustrated. As can be seen in FIG. 5, the fluid channel 7 is formed by utilizing two sections of rubberized cloth 8 and 9 which may be sewn together to form the air channels 7 or sealed with heat and pressure by methods which are well known in the prior art. Thus, in the construction of bladder member there is a continuous outer surface and continuous inner surface each made of thin, flexible rubberized cloth which, when the rib members and axial bridge struts are pressurized, resiliently rigidify the form of the bladder shape.

A connector portion is shown in FIGS. and 2 integrally formed with bladder and extending axially along axis of elongation 12. Connector 11 is of the same construction as bladder 1 and as can be seen in FIGS. 1 and 2, has a plurality of axially extending fluid channels 13 which are in fluid communication with the distal rib 5 at which the bladder transitions into connector portion 11. Axially extending fluid channels 13 are in fluid communication with bridge struts 14 which radially interconnect fluid channels 13. Thus, the network of fluid channels and bridge struts, when pressurized, form the connector portion shape and resiliently rigidify the connection portion when pressurized to form a nominal shape for the connector portion of the bladder. As in the bladder construction, the connector portion is formed by sewing or sealing with heat and pressure rubberized cloth 8 and 9 (refer to FIG. 5) to form the outside and inside surfaces of the connector portion and the air channel 7. By referring to FIG. 8b, the distal cap 16 of the connector portion can be seen releasably and captively held by mask connector 17. The distal cap has inflatable rings 18 which are in fluid communication with axially extending fluid channels 13 and bridge struts 14 forming arcuately shaped ribs which form a cylindrical cap shape; at the distal tip of cap 16, connector ring 19 extends radially beyond inflatable rings 18 forming a lip for enhancing the releasable seal between connector portion 11 and mask connector 17 after the connector portion is inserted into the mask connector.

A inlet check valve 21 is show in FIG. 1 carried in the surface 22 of the bladder at its proximate end. When the bladder is depressed by external force, the air pressure in chamber 22 will increase and close inlet check valve 21; thus, the air contained within the chamber will be forced through the connector portion 11 of the bladder and exhausted through opening 23 located in the distal cap 16 of connector portion 11.

By referring to FIGS. 1, 2 and 3 an air spring or bias tube 24 can be seen which controls the rate at which the bladder 1 after being depressed resumes its nominal shape. In the preferred embodiment shown in FIGS. and 2, air spring 24 has a cylindrical shape and may be made of the rubberized silk cloth material used in the construction of the bladder and the connector portion of the bladder. To control the rate of return of the bladder 1 to its nominal shape, limiting orifices 26 are in fluid communication with rib members 4 and axial bridge struts 6. When bladder 1 is compressed as shown by arrow (A) in FIG. 2, air spring 24 will be compressed and bulge as a result of the increased pressure within air spring chamber 27 causing the air spring to expand as shown in phantom 28. The limiting orifices are so constructed and designed to permit the network of fluid channels forming the structure of the bladder to return to their nominal shape quickly; during the return to nominal shape, inlet check valve 21 will open and ambient air which is at a greater pressure than the pressure within chamber 22 will fill chamber 22 and check valve 21 will close when the pressure is equalized. Thus, not only does air spring 24 control the rate at which ambient air will fill the bladder 1, it will also act to stabilize the shape of the network of fluid channels. The construction of air spring 24 is more clearly shown in FIG. 3 which is an enlargement of area 3 shown on FIG. 2. In referring to FIG. 3, ribs 4' are in fluid communication with air spring chamber 27 to permit air spring chamber 27 to be pressurized with air simultaneously with the pressurization of the fluid channel network. Thus, when the bladder is compressed in the direction of arrow (A) as shown in FIG. 2, the pressure will increase within air spring chamber 27 above the equilibrium pressure of the fluid channel network when the bladder is depressed from its nominal shape; when the depressing force is removed the air spring will return to the equilibrium shape and the rate at which it will return to the equilibrium shape will be determined by the dimensions of limiting orifices 26.

By referring to FIG. 6, the preferred embodiment of the mask device of this invention can be seen in perspective. Mask device 28 is composed of two integrally connected portions, namely, a mask connector receptacle portion 29 and a face portion 31. As in the bladder construction, the mask device is shaped by a network of fluid channels which are in fluid communication such that when pressurized form the mask connector portion nominal shape and the nominal shape of the face portion 31. A triangularly shaped fluid channel or rib 32 is integrally formed in a clear flexible plastic material which is used for constructing the face portion 31. This permits the user of the resuscitation device to see the patient's face when administering resuscitation. The cavity 33 of the face portion 31 of the mask device communicates with mask connector 29 to permit air which is pumped from the bladder to flow to the patient. A flapper valve 34 is shown in FIGS. 10(A) and 10(B) which in the preferred embodiment is located in the mask connector or receptacle 29 and which functions so as to permit air flow into the face portion 3 of the mask device when the bladder 1 is compressed, and to close when the bladder depressing force is released. Referring again to face portion 31 as shown in FIG. 6, triangularly shaped rib 32 is interconnected to and in fluid communication with rib spars 36 and 37 which when pressurized resiliently rigidify the mask shape; similarly, lateral ribs 38 and 39 are in fluid communication with triangularly shaped rib 32 and rib spars 36 and 37 and form the network structure of the shape of the face portion 31 of the mask device. The mask device is separately inflatable from the bladder by compressed air canister 41.

Figure 7:
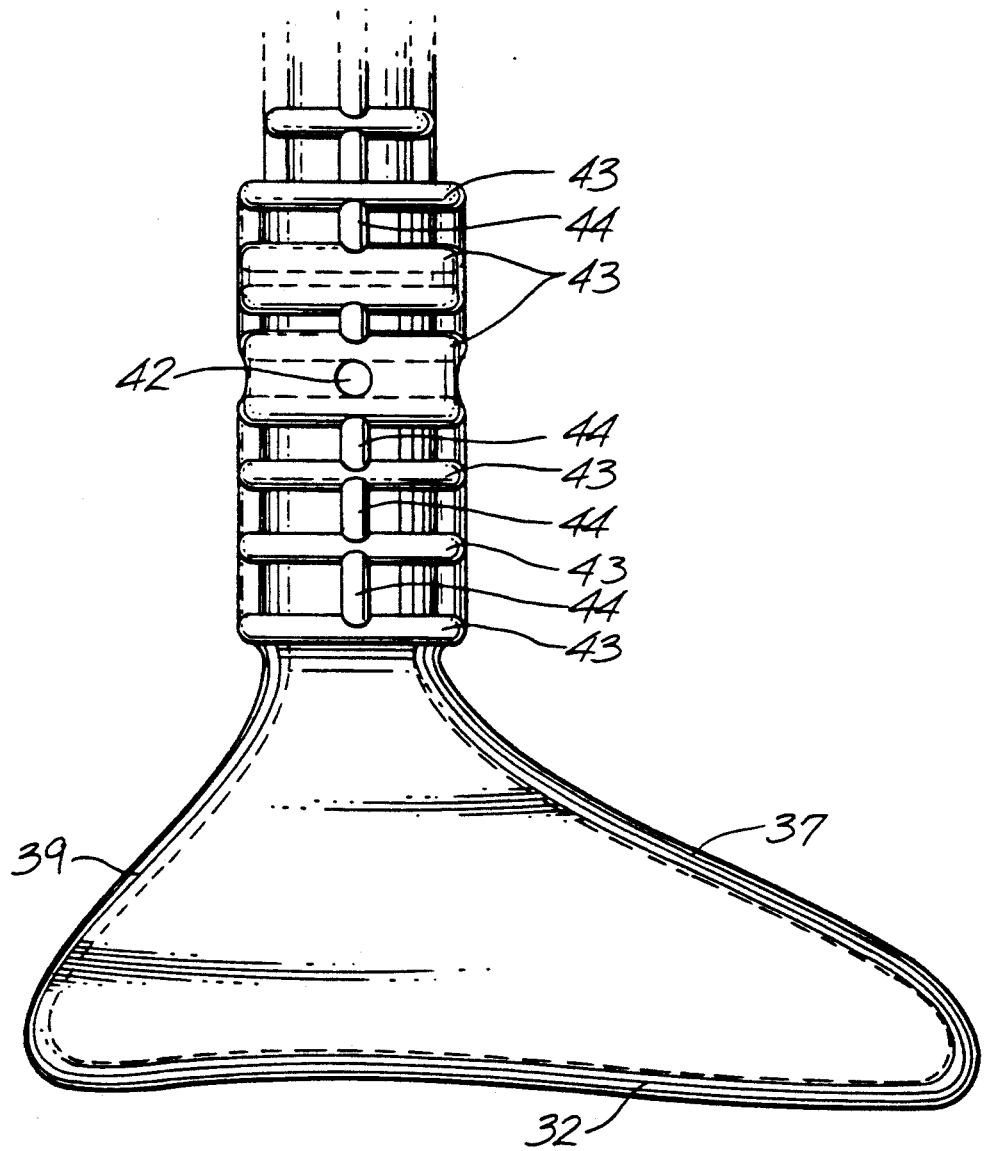
FIG. 7 is a left side elevation view of FIG. 6.
Figure 8A:
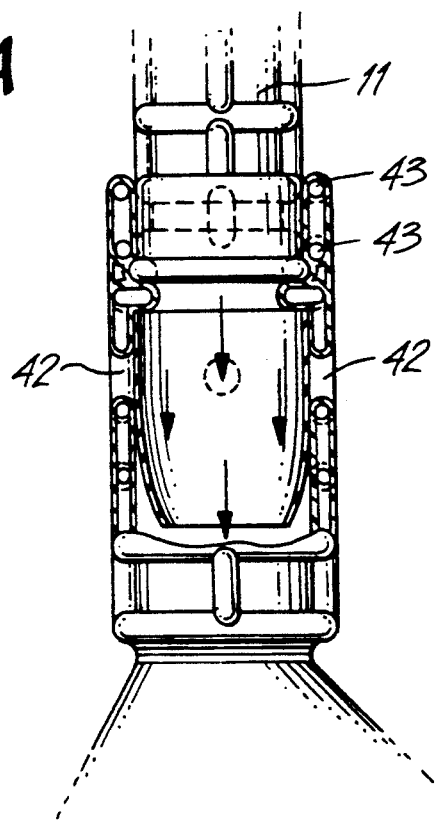
FIG. 8A is an illustration of a flapper valve contained in the connector portion in an open position.
Figure 8B:
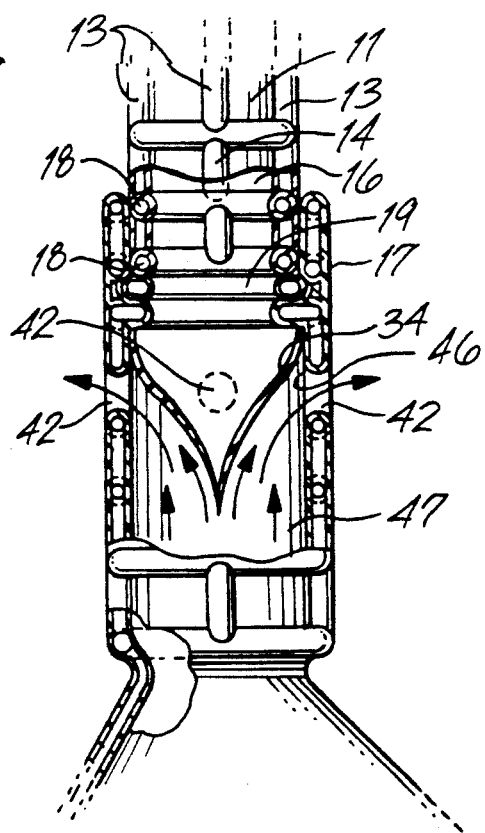
FIG. 8B is an illustration of the flapper valve shown in FIG. 8A in a closed position.

In FIG. 6, the mask connector or receptacle is shown in perspective. To exhaust exhaled air from the patient, mask connector 29 has a plurality of exhaust ports 42. By referring to FIGS. 7, 8(A) and 8(B) the structure of mask connector 29 can be seen. Referring to FIG. 7, inflatable mask rings 43 are shown to be interconnected through a plurality of bridge struts 44 which provide fluid communication between rings 43; and through rings 43 the struts are in fluid communication with rib spars 36 and 37 and lateral ribs 38 and 39. Flapper valve 34 may be bonded or sewn to the inner wall 46 which forms the boundary of the conduit cavity 47 contained within mask connector or receptacle 29. As can be seen in FIGS. 8(A), 8(B), 10(A) and 10(B), flapper valve 34 is made of a thin latex-type material which collapses against itself when air is sucked through conduit cavity 47 by the relative vacuum caused by bladder returning to its nominal position after being depressed; the sucked air exhausting through exhaust ports 42 when flapper valve 34 is collapsed upon itself. Referring to FIGS. 8(A) and 10(A), when the bladder 1 is compressed, air is pumped from the bladder under pressure and the flapper valve opens thereby closing exhaust ports 42 and permitting air flow into the mask. In the preferred embodiment, the flapper valve is made of a flexible material such as plastic, rubber, cloth or a combination of these and less than 10 mm in thickness.

Figure 10:
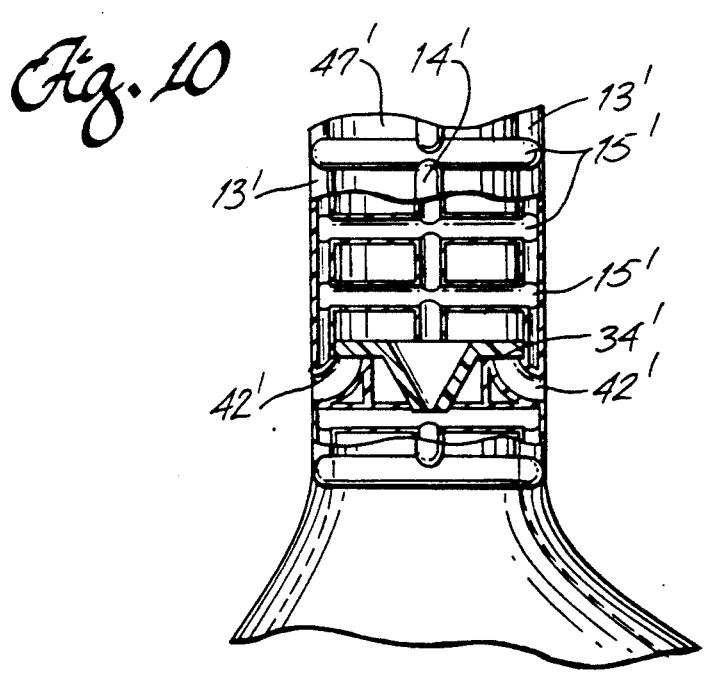
FIG. 10 is a partial cross-sectional view of FIG. 9 illustrating the outlet check valve controlling air flow into and from the mask device.
Figure 10A:
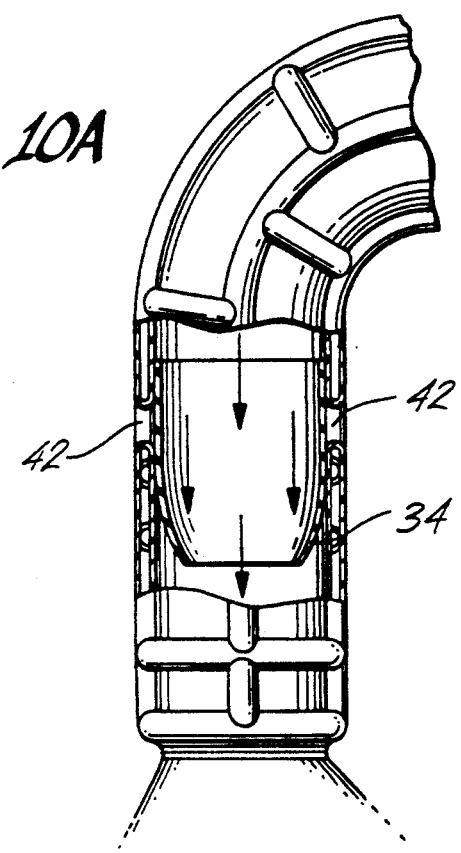
FIG. 10A is a preferred outlet check valve of this invention and is shown in an open position.
Figure 10B:
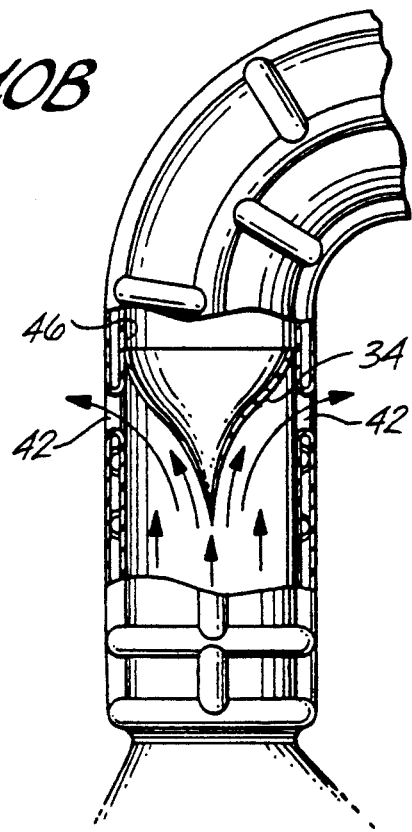
FIG. 10B is the preferred outlet check valve shown in a closed position.

Another embodiment of this invention is disclosed in FIGS. 9 and 10. In this embodiment, the bladder 1' and the mask device 28' are integrally joined together to form a one-piece resuscitation device. As in the embodiment above-described, this embodiment comprises a network of fluid channels 2' which are in fluid communication with each other and when pressurized resiliently rigidify to establish a nominal erected bladder shape and a nominal erected mask shape. The network of fluid channels 2' is composed of a plurality of rib members 4' and axial bridge struts 6' where the resuscitator device illustrated in FIG. 9 has an axis of elongation 12'. The method of construction of rib members 4' and axial bridge struts 6' in this embodiment is identical to the method of construction utilized in the preferred embodiment which is illustrated in FIG. 5. Referring again to FIG. 9, the connection transition between the bladder 1' and the mask 28' has axially extending fluid channels 13' and bridge struts 14' which are in fluid communication with rib spars 37' and 39'. Axially extending fluid channels 13' extend to and become integrally part of bridge spars 36' and 37' and lateral ribs 38' and 39' which in turn are in fluid forms the bearing surface for the mask device. A plurality of inflatable rings 15' are in fluid communication with axially extending fluid channels 13' and are interconnected by inflatable bridge struts 14' such that upon pressurization form a transition structure from the bladder 1' to the mask 28.' Conduit cavity 47' is contained within the transition structure for directing air which has been pumped from bladder 1' to the mask 28'. An exhaust shuttle flapper valve is positioned intermediate the bladder 1' and mask device 28' to control the flow of air to the mask. Exhaust ports 42' are located adjacent the flapper valve and are closed when air is forced through conduit cavity 47' towards the mask 28' and are open to exhaust air from the patient as the bladder returns to its original nominal shape after being depressed. After the bladder 1' is released, the nominal bladder shape is biased by an internal air spring or bias tube (not shown in FIG. 9) in the same manner as bias tube or air spring 34 described in the preferred embodiment of FIG. 1 returned the bladder to its nominal shape; this creates a vacuum and sucks ambient air back into the air chamber 22'. To effectively administer artificial respiration, the resuscitator must refill with air in approximately five seconds or less and should contain approximately 1.8 liters of air.

Thus, a device has been described which is made of a thin medical grade plastic that is extremely flexible. An integral network of interconnected air passageways has been presented which when pressurized by a compressed air cylinder, resiliently rigidify both the bladder and the mask to establish nominal shapes. The resuscitator of this invention does not require ambient air pressure to return the bladder and mask to their original shapes; this is achieved by utilizing an internal air spring or bias tube which is in fluid communication with certain rib members and the axial bridge struts between those members. The air struts and ribs contain limiting orifices which control the rate at which the bladder and mask return to their original shapes and in so doing cause a vacuum to occur in the bladder air chamber. The quick recovery cycle provided by the air spring allows the resuscitator to used for emergency resuscitation.

While I have shown and described certain embodiments of the present safety valve device, it is to be understood that it is subject to many modifications without departing from the spirit and scope of the claims as recited herein.

What is claimed is:

1. An improved pulmonary resuscitator of the type having a compressible bladder to be compressed to supply air to a user device, said bladder having a flexible wall and an inlet check valve and said user device having outlet check valve, wherein the improvement comprises:
   a) a first network means comprising substantially orthogonal interconnected inflatable fluid channels integrally contained in said flexible wall said first network means upon inflation erecting said bladder and maintaining said bladder erect and resilient during compression of said bladder;
   b) means carried by said bladder for inflating said first network of inflatable fluid channels with a gas and sealingly retaining said gas within said network during compression of said bladder.

2. The improved pulmonary resuscitator recited in claim 1 wherein said pulmonary resuscifator has an axis of elongation and said first network of interconnected inflatable channels comprises a network of inflatable tubes radially spaced from said axis and axially spaced with respect to said axis.

3. The improved pulmonary resuscitator recited in claim 1 wherein said bladder is made of a flexible plastic.

4. The improved pulmonary resuscitator recited in claim 1 wherein said bladder is made of a flexible rubberized cloth material.

5. The improved pulmonary resusictiator recited in claim 1 wherein said user device is a face mask to be fitted over the face of a person to be revived comprising:
   a) a thin wall body made of a flexible plastic material;
   b) a second network of interconnected inflatable fluid channels integrally contained within said body wall where said network of fluid channels when inflated erect said body into a face mask shape and maintain said body erect and resilient;
   c) a third network of interconnected inflatable fluid channels integrally contained within said body wall and integrally interconnected with said second network of inflatable fluid channels where said third network inflates upon inflation of said second network and when inflated erected and maintains a recepticle extending from said face mask to permit the passage of air to the user;
   d) means carried by said body for inflating said second and third networks of inflatable fluid channels with a gas and sealingly retaining said gas within said second and third inflatable fluid channels.

6. The improved pulmonary resuscitator recited in claim 5 wherein said pulmonary resuscitator has an axis of elongation and where said networks of second and third inflatable fluid channels comprise a network of inflatable tubes radially spaced from said axis and axially spaced with respect to said axis.

7. An improved pulmonary resuscitator recited in claim 5 wherein said outlet check valve comprises a flapper valve adapted to permit the flow of air into said mask upon comrpession of said bladder, and for venting said air from said mask after said bladder has been compressed, said mask having an exhaust port located adjacent said flapper valve such that said exhaust port is closed by said flapper valve when said bladder is compressed and open when said flapper valve closes.

8. The improved pulmonary resuscitator recited in claim 5 wherein said mask is made of a clear flexible plastic material.

9. The improved pulmonary resuscitator recited in claim 1 further comprising inflatable bias means disposed within said bladder and sealingly interconnected to said first network of interconnected inflatable fluid channels and in exclusive fluid communication with said first network of interconnected inflatable fluid channels for biasing said bladder to maintain said bladder erect and resilient during the compression of said bladder.

10. An improved omnidirectional compressible bladder having an inlet port to be compressed to supply air to a user device comprising:
    a) a body having a thin wall made of a flexible plastic material having an exhaust port;
    b) a first network means comprising substantially orthogonal interconnected inflatable fluid channels integrally contained in said flexible wall said first network means for inflatably erecting said bladder and maintains said bladder erect and resilient during compression of said bladder; and
    c) means carried by the bladder for inflating said first network of inflatable fluid channels with a gas and sealingly retaining said gas within said network during compression of said bladder.

11. The compressible bladder recited in claim 10 further comprising inflatable bias means disposed within said bladder and sealingly interconnected to said first network of interconnected inflatable fluid channels and in exclusive fluid communication with said first network of inflatable fluid channels for biasing said bladder to maintain said bladder erect and resilient during the compression of said bladder.

12. The compressible bladder recited in claim 11 wherein said inflatable bias means comprises a bias tube integrally and sealingly interconnecting said first network of inflatable fluid channels having a limiting orifice in exclusive fluid communication with said first network of inflatable fluid channels and so disposed within said bladder such that upon inflation of said first network of inflatable fluid channels said bias tube will resiliently erect to from a nominal erected tube shape in fluid equibilrum with said erected bladder whereby upon compression of said bladder fluid pressure within said bias tube will increase thereby biasing said bladder to remain erect and resilient.

13. An inflatable face mask for use in pulmonary resuscitation comprising:
    a) a thin wall body made of a flexible plastic material;
    b) a second network of interconnected inflatable fluid channels integrally contained within said body wall where said network of fluid channels when inflated erect said body into a face mask shape and maintain said body erect and resilient;
    c) a third network of interconnected inflatable fluid channels integrally contained within said body wall and integrally interconnected with said second network of inflatable fluid channels where said third network inflates upon inflation of said second network and when inflated erects and maintains a recepticle extending from said face mask to permit the passage of air to the user;

d) means carried by said body for inflating said second network and said third network of inflatable fluid channels with a gas and sealingly retaining said gas within said second and third inflatable fluid channels.

14. The inflatable face mask recited in claim 13 where said flexible valve means comprises a flapper valve sealingly contained within said body adjacent said exhaust port.

15. The inflatable face mask recited in claim 13 where said body has an axis of elongation and where said third network of interconnected inflatable fluid channels comprises a network of inflatable tubes in fluid communication radially and axially spaced with respect to said axis defining a continuous fluid passage.

16. An improved pulmonary resuscitator of the type having a compressible bladder to be compressed to supply air to a face mask fitted over the face of a person to be revived, the improvement comprising:

a) a first network means comprising interconnected inflatable fluid channels integral with the bladder said first network means upon inflation erecting the bladder and maintaining the bladder erect and risilient;

b) a second network of interconnected fluid channels integral with the face mask to erect it when the bladder is erected;

c) means to interconnect the fluid channels of the bladder with those of the face mask;

d) means to inflate the fluid channels with a gaseous medium to erect the bladder and face mask and to maintain gas pressure in the fluid channels during use of the resuscitator; and e) an inlet check valve to the bladder to admit air whereby the gaseous medium admitted into the bladder channels erects the bladder and face mask for use and after each pump of the bladder erects the bladder to draw ambient air into it through the inlet valve for the next cycle.

17. The improved pulmonary resuscitator recited in claim 16 further comprising inflatable bias means disposed within said bladder and sealingly interconnected to said first network of interconnected fluid channels and in exclusive fluid communication with said first network of inflatable fluid channels for biasing said bladder to maintain said bladder erect and resilient during compression and expansion of the bladder.

18. The improved pulmonary resuscitator recited in claim 17 wherein said inflatable bias means comprises a bias tube made of a flexible material and having a limiting orifice in fluid communication with said first network of inflatable fluid channels and so disposed within said bladder such that upon inflation of said first network of inflatable fluid channels said bias tube will resiliently erect to form an erected tube shape in fluid equibilirum with said first network of inflatable fluid channels such that upon compression of said bladder fluid pressure within said bias tube will increase thereby biasing said bladder to remain erect and resilient.

* * * * *